(12) United States Patent
Silva et al.

(10) Patent No.: US 7,521,569 B2
(45) Date of Patent: Apr. 21, 2009

(54) PROCESS TO OBTAIN DIBENZYLBUTYROLACTONIC LIGNANS, PROCESS TO OBTAIN SYNTHETIC DERIVATIVES FROM LIGNANS BEARING ANTI-CHAGAS CHEMOPROPHYLACTIC AND THERAPEUTICAL ACTIVITIES

(75) Inventors: Marcio Luis Andrade Silva, Franca (BR); Sergio Albuquerque, Ribeirao Preto (BR); Gustavo Henrique Bianco Souza, Pedregulho (BR); Jairo Kenupp Bastos, Ribeirao Preto (BR); Rosangela Silva, Jaboticabal (BR)

(73) Assignee: Fundação De Amparo À Pesquisa Do Estado de São Paulo, São Paulo (BR)

( * ) Notice: Subject to any disclaimer, the term of this patent is extended or adjusted under 35 U.S.C. 154(b) by 0 days.

(21) Appl. No.: 11/951,460

(22) Filed: Dec. 6, 2007

(65) Prior Publication Data
US 2008/0090901 A1  Apr. 17, 2008

Related U.S. Application Data

(62) Division of application No. 10/508,875, filed as application No. PCT/BR03/00045 on Mar. 25, 2003, now Pat. No. 7,317,114.

(30) Foreign Application Priority Data
Mar. 25, 2002 (BR) .................... 0201237

(51) Int. Cl.
C07D 305/12 (2006.01)
C07D 307/00 (2006.01)
(52) U.S. Cl. ..................... 549/435; 549/320
(58) Field of Classification Search ........... 549/435; 514/464
See application file for complete search history.

(56) References Cited

FOREIGN PATENT DOCUMENTS

WO    WO 8900160    *  1/1989

OTHER PUBLICATIONS

Rehnberg et al. Journal of Organic Chemistry, 1990, 55, 4340-4349.*
Badheka et al., Dibenzylbutyrolactone Lignans from *Piper cubeba*, Phytochemistry, 25, 487-489, 1986.
Badheka et al., Lignans from *Piper cubeba*. Part 3. Lignans of *Piper cubeba*. Phytochemistry 1987, 26(7), 2033-6 (Eng). Columbus, Ohio, USA: Chemical Abstracts, vol. 108, Feb. 1, 1988, p. 417, col. 1, the abstract No. 52748t.
Bastos et al., Isolation of lignans and sesquiterpenoids from leaves of *Zanthoxylum naranjillo*. Nat.Prod.Lett. 1996, 9(1), 65-70 (Eng). Columbus Ohio, USA: Chemical Abstracts, vol. 126, No. 12 Mar. 24, 1997, p. 325, col. 2, the abstract No. 155086b.
Silva et al., Evaluation of *Piper cubeba* Extract, (-)-Cubebin and its Semi-synthetic Derivatives against Oral Pathogens, Phytotherapy Research, 2007 21(5), pp. 420-422.

* cited by examiner

*Primary Examiner*—D. Margaret Seaman
*Assistant Examiner*—Nizal S Chandrakumar
(74) *Attorney, Agent, or Firm*—Volpe and Koenig, P.C.

(57) ABSTRACT

The invention refers to a process to obtain lignans, especially to obtain cubebin and methylpluviatolide from leaves of *Zanthoxylum naranjillo* or *Piper cubeba*. It also refers to a process to obtain semi-synthetic derivatives of cubebin, especially dibenzylbutirloactonic lignans, such as: hinokinin, o-acetyl cubebin, o-methyl cubebin, 6, 6'-dinitrohinokinin and o-dimethylethylamine cubebin and other derivatives which may be obtained, as well as to obtain methylpluviatolide derivatives, which are used to manufacture drugs to provide activity at least five times higher than observed for gentian violet and other compounds used heretofore for blood treatment and Chagas' disease prophylaxis.

2 Claims, 1 Drawing Sheet

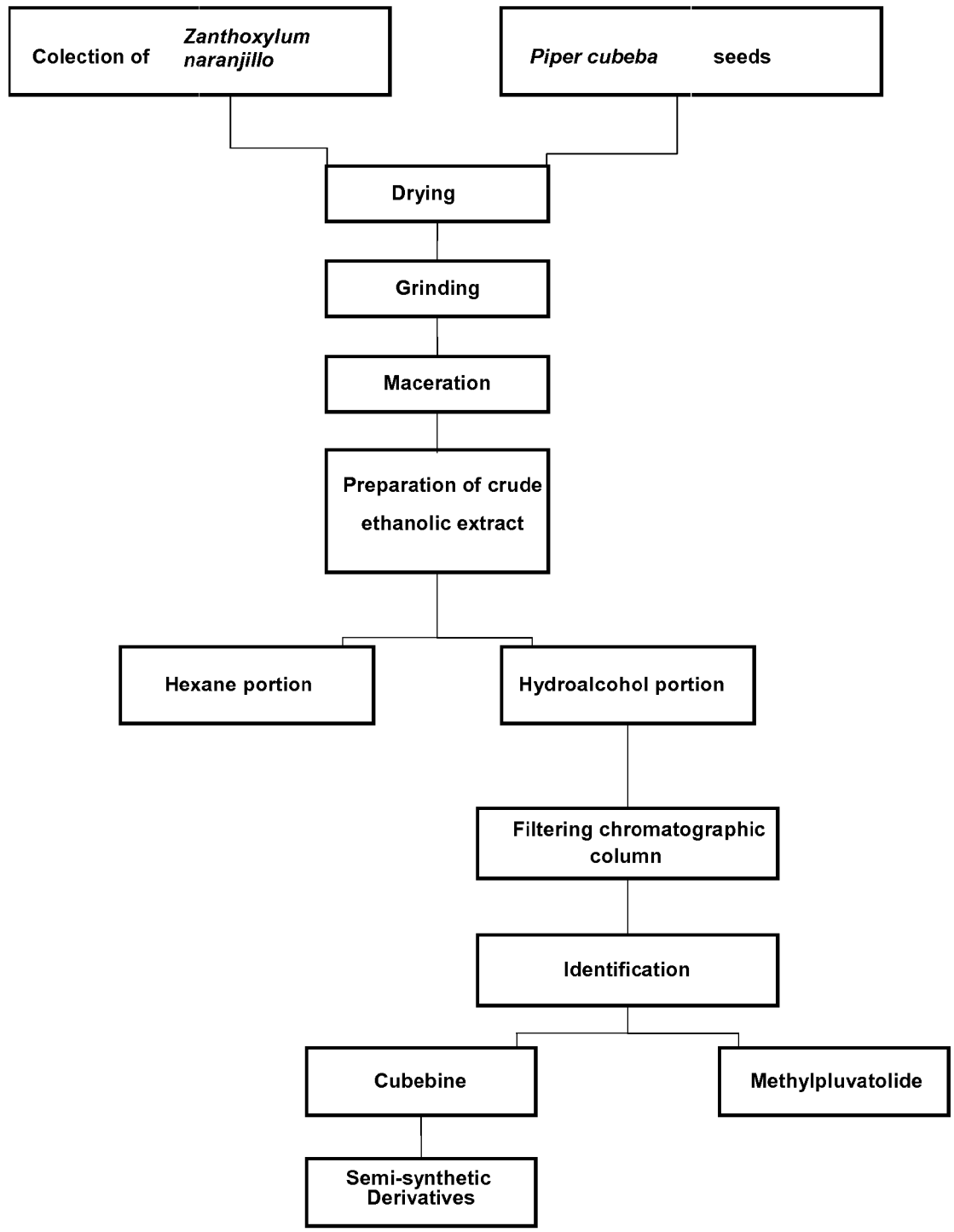

PROCESS TO OBTAIN DIBENZYLBUTYROLACTONIC LIGNANS, PROCESS TO OBTAIN SYNTHETIC DERIVATIVES FROM LIGNANS BEARING ANTI-CHAGAS CHEMOPROPHYLACTIC AND THERAPEUTICAL ACTIVITIES

CROSS REFERENCE TO RELATED APPLICATIONS

This application is a division of U.S. patent application Ser. No. 10/508,875, filed Sep. 23, 2004, which is a U.S. National Phase of PCT/BR03/00045, filed on Mar. 25, 2003, both of which are incorporated by reference as if fully set forth.

FIELD OF THE INVENTION

The invention refers to a process to obtain lignans, especially to obtain cubebin and methylpluviatolide from leaves of *Zanthoxylum naranjillo* or *Piper cubeba*. It also refers to a process to obtain semi-synthetic derivatives of cubebin, especially dibenzylbutyrolactonic lignans, such as: hinokinin, o-acetyl cubebin, o-methyl cubebin, 6, 6'-dinitrohinokinin and o-dimethylethylamine cubebin and other derivatives which may be obtained, as well as to obtain methylpluviatolide derivatives, which are used to manufacture drugs to provide activity at least five times higher than observed for gentian violet and other compounds used heretofore for blood treatment and Chagas' disease prophylaxis.

BACKGROUND OF THE INVENTION

The use of medicinal plants with therapeutical purposes goes back to the beginning of civilization, when men found to be in need and started a long course of handling, adapting and modifying natural resources for their own benefit. Still today, a large portion of the population, especially low-income people, makes use of this ancient art as the main resource for maintenance and to alleviate illnesses.

In this context, etnopharmacology acts as a very important tool for the study and research of new drugs of vegetal origin, since the molecular diversity of the vegetal kingdom is still considered as unlimited, despite scientific advancements. Furthermore, as products from those organisms are very similar to mammals' metabolism, natural products often show various biological properties due to possible action over recipients within mammals' organisms.

With technological development, deeper studies have shown to researchers and the pharmaceutical industry the need to synthesize bioactive substances, having natural products as their raw materials. Numerous classes of different natural products have been employed so to synthesize new drugs. As an example, there are terpene derivatives used as raw materials for the synthesis of artemisin, a sesquiterpene derivative with important anti-malaria activities. The class of lignans, in which cubebin is included, is considered very interesting since, besides the activities as already mentioned, they present anti-tumor and anti-viral activities. In a study written by Yang in 1996, isolated lignans from the species *Trachelospermum gracilipes* (Apocynacea) had evaluated their anti-HIV activity in vitro and results have shown that virus replication was inhibited in infected H9 cells.

Chagas' disease was defined in the American Continent in 1909. The agent causing the disease is *Trypanosoma cruzi* and affects more than 18 million people in the continent, causing about 400,000 deaths each year. In Brazil, a study of effected in the City of Londrina (Parana) in 1995 presented a statistic showing that 834×7 to 14 year-old children have shown positive serology for Chagas' Disease. Therefore, research for agents showing tripanocidal activity is still required. In the American continent, the occurrence of human infection by *T. cruzi* is estimated at 16 to 18 million cases. However, additional 90 million, i. e. 25% of the continent population are exposed to the risk of being infected. Among 211 million inhabitants in the south corner of the American continent, 11 million people are infected and about 54 million are in risk of being infected, thus representing 31% of the population. According to the World Health Organization, more than 50,000 people die each year due to the Chagas' disease.

A study with older than 74-year old people in the region of Ribeirao Preto, State of Sao Paulo, has disclosed that 13% of heart diseases are a consequence of "Chagas' Disease".

The main solution to avoid the disease is still to combat triatomine, while contamination by blood transfusion can be avoided by the serologic test of the donator or by adding gentian violet to infected blood.

An important review of natural active principles with tripanocidal activity was published in 1996. Various classes of secondary metabolites are included in the bibliographic review, but no metabolite included in lignans has been included. However, a recently published document by our group has observed that various dibenzylbutyrolactonic lignans showed significant tripanocidal activity, thus making evaluation of cubebin derivatives against Chagas' disease become promising.

During effected research, we have found that isolated lignans of *Zanthoxylum naranjillo*, such as methylpluviatolide and cubebin, as well as semi-synthetic derivatives hinokinin, o-acetyl cubebin, o-methyl cubebin, 6, 6'-dinitroinoquinin and o-dimethylethylamine cubebin bear anti-Chagas activity.

Concerning cubebin, only one patent associated to prophylactic and therapeutical activity in kidney diseases has been found (JP 01180824-A; International Classification: A61K-031/36; C07D-407/14), dated Jul. 18, 1989.

SUMMARY OF THE INVENTION

Due to the above disclosure, the object of the invention as proposed herein is to obtain cubebin and methylpluviatolide from leaves of *Zanthoxylum naranjillo* or *Piper cubeba* and semi-synthetic cubebin derivatives, dibenzylbutyrolactonic lignans: hinokinin, o-acetyl cubebin, o-methyl cubebin, 6, 6'-dinitrohinokinin and o-dimethylethylamine cubebin and other derivatives which may be obtained, as well as methylpluviatolide derivatives, by means of processes as described herein, which will be used to manufacture drugs to provide activity at least five times higher than observed for gentian violet and other compounds used heretofore for blood treatment and Chagas' disease prophylaxis.

One embodiment of the invention is directed to a process for obtaining a synthetic lignan derivative of the structural formula (5):

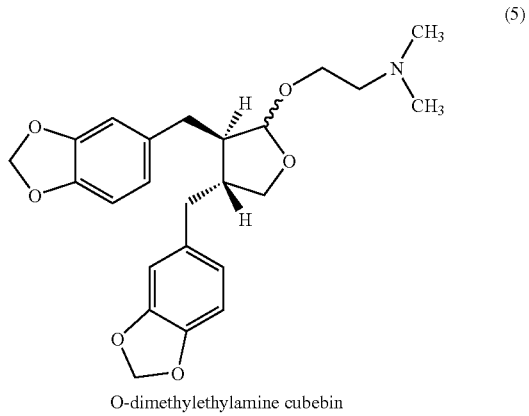

O-dimethylethylamine cubebin (5)

from the (–)-cubebin derivative of the structural formula (1):

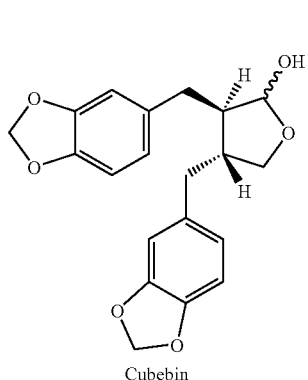

Cubebin (1)

The process includes the steps of (a) reacting (–)-cubebin with dimethylethylamine chloride in sodium ethoxide, followed by the addition of dimethylethylamine chloride under reflux to form a reaction medium; (b) chromatographic analysis of the reaction medium following the reaction; (c) isolating (–)-O-dimethylethylamine-cubebin (5) from the reaction medium by adding water and powdered NaHCO3 up to the alkalization point of the reaction medium (pH=9 to 10) followed by extraction with ethyl acetate; and (d) transferring the organic phase of the reaction medium to a collecting flask followed by purification under preparative circular chromatography [CCP] (CROMATOTRON).

DETAILED DESCRIPTION OF THE DRAWINGS

For better understanding of the invention as proposed herein,

FIG. 1 shows a fluxogram of the process to obtain lignans from *Zanthoxylum naranjillo* and *Piper cubeba*.

DETAILED DESCRIPTION OF THE INVENTION

As we can see from FIG. 1, the process to obtain cubebin (1), lignan, with structural formula:

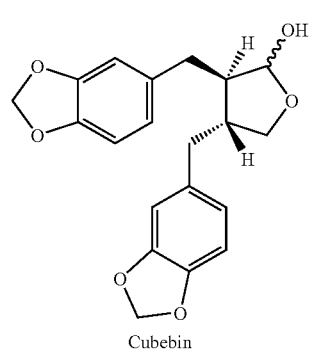

Cubebin (1)

and the lignan methylpluviatolide (2) with structural formula:

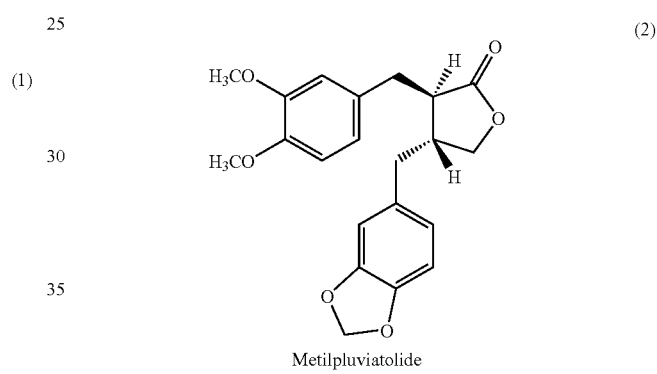

Metilpluviatolide (2)

from *Zanthoxylum naranjillo* includes the following stages:

a) collection and oven-drying *Zanthoxylum naranjillo* leaves at a temperature from 35 to 55° C.;

b) grinding *Zanthoxylum naranjillo* leaves in a knife grinder;

c) maceration of the powder obtained from *Zanthoxylum naranjillo* leaves and exhaustive extraction with hexane at 25° C. for about five days;

d) preparation of the gross extract from filtering the maceration product and concentrating it under reduced pressure at the temperature of 30° C. until the full elimination of solvent;

e) repeated purification of the gross extract obtained from *Zanthoxylum naranjillo* leaves in a chromatographic column over silica gel and elution with a solvent system starting with hexane, AcOEt (AcOEt) and ethanol under growing proportions, supplying 210 chromatographic portions of 500 ml each.

f) obtaining and isolation of cubebin (1) and methylpluviatolide (2) from chromatographic portions by crystallization (hexane/acetone (Me2CO, 4:1) or preparative chromatography with slender layer (hexane/Me2CO, 4:1).

g) identification made by 1H and 13C nuclear magnetic resonance (NMR) data analysis [α]D, Mass, IV.

This procedure has allowed to obtain cubebin (1) and methylpluviatolide (2).

Similarly, the process to obtain cubebin from *Piper cubeba*, which fluxogram has also been shown by FIG. 1, includes the following stages:

a) grinding *Piper cubeba* seeds in a knife grinder;

b) maceration of the powder obtained from *Piper cubeba* seeds and exhaustive extraction with 90% ethanol for 72 h cycles;

c) preparation of the gross extract from filtering the maceration product and concentrating it under reduced pressure at the temperature of 40° C. until the full elimination of solvent;

d) solubilization of the crude ethanol extract in a 9:1 hydroalcoholic solution of methanol and partition with n-hexane so to eliminate the terpene oil portion;

e) separation of the hydroalcoholic portion and later concentration until fully eliminating solvents;

f) realization of liquid chromatography under vacuum over silica gel of the crude hydroalcoholic portion, by using the following solvent systems: 100% hexane, 50% hexane: dichloromethane; 100% dichloromethane; 50% dichloromethane: ethyl acetate and 100% ethyl acetate.

g) elimination of solvent under vacuum from the portion in 100% dichloromethane and its successive recrystallizations in 4:1 hexane:acetone for cubebin (1) purification;

h) purity analysis of cubebin as crystallized under slender layer chromatography and high efficiency liquid chromatography.

Obtaining Cubebin Derivatives

I) O-acetyl Cubebin

A) Reaction of cubebin with acetic anhydride in pyridine (in a microscale, we have: 50 mg of cubebin reacting with 3 ml of anhydride in 0.3 ml of pyridine [10% of volume], shaking at room temperature for 24 h);

B) chromatographic analysis to follow the reaction;

C) isolation of o-acetyl cubebin by addition of toluene made to fully eliminate pyridine from the medium;

D) addition of dichloromethane and successive evaporations under reduced pressure to eliminate toluene;

E) the organic phase was therefore transferred to a collecting flask and purification under preparative circular chromatography has followed [CCP] (CROMATOTRON);

F) after this procedure, the product (3) has been submitted to purity determination by high efficiency liquid chromatography (CLAE), finding a purity index >95%; the product (acetyl cubebin) was taken for 1H and 13C NMR analysis and [α]D26.

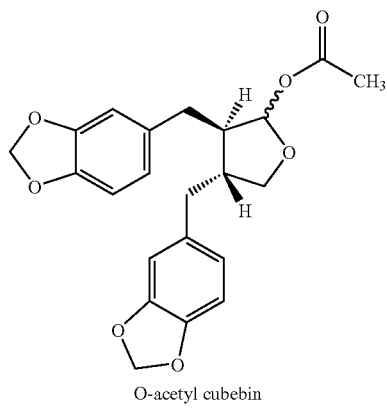

O-acetyl cubebin

II) O-methyl Cubebin

G) Reaction of cubebin with methyl iodide in dry THF and NaH (in a microscale, we have: cubebin in dry THF, addition of NaH (1 g) and shaking for ½ hour at room temperature; afterwards, methyl iodide has been added and was reacted for one night under N2 atmosphere);

H) chromatographic analysis to follow the reaction;

I) the isolation of o-methyl cubebin has been made: (1) by decomposition of NaH in excess by the addition of methanol in water (1:1), subsequent addition of diluted HCl and extraction with ethyl acetate; (2) neutralization of the organic phase obtained with a 5% NaHCO3 solution, NaCl saline solution (10%) and 5% NaHCO3 solution; and (3) drying the medium with anhydrous MgSO4;

J) silica gel column chromatography using 4:1 hexane: ethyl acetate as eluent;

K) the organic phase was therefore transferred to a collecting flask and purification under preparative circular chromatography has followed [CCP] (CROMATOTRON);

L) after this procedure, the product (4) has been submitted to purity determination by high efficiency liquid chromatography (CLAE), finding a purity index >95%. the product (methyl cubebin) was taken for 1H and 13C NMR analysis and [α]D26;

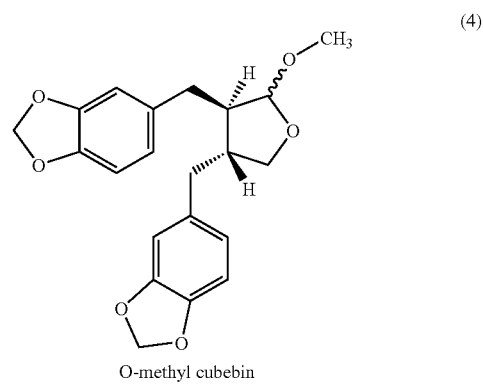

O-methyl cubebin

III) O-dimethylethylamino Cubebin

M) Reaction of cubebin dimethylethylamine chloride in sodium ethoxide (in microscale, we have: 50 mg of cubebin in sodium ethoxide (2 hour reflux); subsequent addition of dimethylethylamine chloride staying in reflux for over five hours);

N) chromatographic analysis to follow the reaction;

O) isolation of cubebin o-dimethylethylamine was made by pouring reactional medium over 30 ml of water and adding powdered NaHCO3 until alkalinizing the medium (pH=9 to 10) and extraction with ethyl acetate;

P) the organic phase was therefore transferred to a collecting flask and purification under preparative circular chromatography has followed [CCP] (CROMATOTRON);

Q) after this procedure, the product (5) has been submitted to purity determination by high efficiency liquid chromatography (CLAE), finding a purity index >95%. the product (dimethylethylamine cubebin) was taken for 1H and 13C NMR analysis and [α]D26;

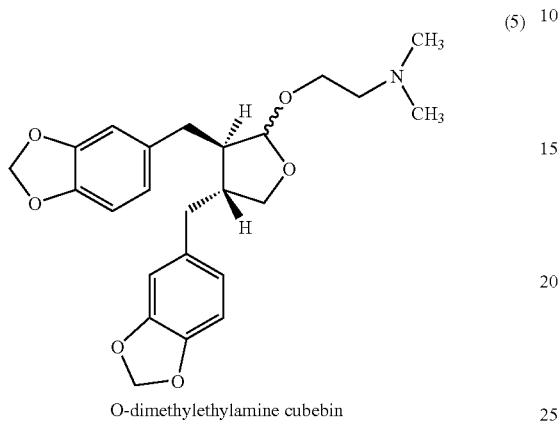

O-dimethylethylamine cubebin (5)

IV) Hinokinin

R) reaction of cubebin with PCC in dry dichloromethane (in a microscale, we have: 50 mg de cubebin in a flask containing dry dichloromethane and sealed under inert atmosphere (N2). In a three-beak balloon, also under inert atmosphere, 1 Mol Eq of pcc in dry dichloromethane has been added; the cubebin solution in DCM is added by means of a hypodermic syringe, always maintaining the inert atmosphere for 24 hours, temperature of –6° C. and under constant shaking);

S) chromatographic analysis to follow the reaction;

T) the isolation of hinokinin was made by: 1) pouring the reaction medium in a chromatographic column (under vacuum) with sinterized plaque n° 2 containing monohydrated MgSO4 by providing vacuum filtration; 2) submitting the sample to a chromatographic column with silica gel 60 and the following solvent gradient system: 100% hexane, 8:2 hexane: ethyl acetate, 7:3 hexane: ethyl acetate, 6:4 hexane: ethyl acetate, 100% ethyl acetate and 100% methanol;

U) the organic phase was therefore transferred to a collecting flask and purification under preparative circular chromatography has followed [CCP] (CROMATOTRON);

V) after this procedure, the product (6) has been submitted to purity determination by high efficiency liquid chromatography (CLAE), finding a purity index >95%. the product (hinokinin) was taken for 1H and 13C NMR analysis and [α]D26;

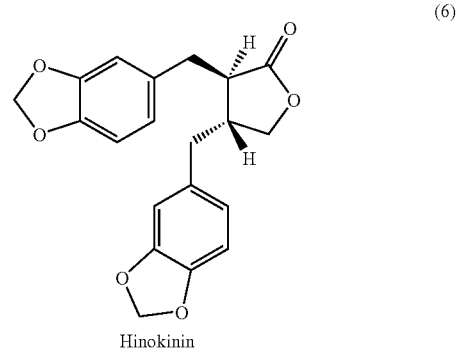

Hinokinin (6)

V) 6, 6'-Dinitrohinokinin

W) Reaction between hinokinin and nitric acid in chloroform (in microscale we have: 50 mg of hinokinin in chloroform by keeping the reaction medium at –6° C., adding 6 Mol Eq of nitric acid dropwise and slowly, keeping the reaction under the same conditions and with constant shaking for two hours, after which a saturated Na2CO3 solution was added to finish it);

X) chromatographic analysis to follow the reaction;

Y) isolation of 6, 6'-dinitrohinokinin was made by: 1) extraction of the reaction medium with chloroform and subsequent evaporation under reduced pressure; 2) recrystallizations under methanol;

Z) the organic phase was therefore transferred to a collecting flask and purification under preparative circular chromatography has followed [CCP] (CROMATOTRON);

AA) after this procedure, the product (7) has been submitted to purity determination by high efficiency liquid chromatography (CLAE), finding a purity index >95%. the product (6, 6'-dinitrohinokinin) was taken for 1H and 13C NMR analysis and [α]D26;

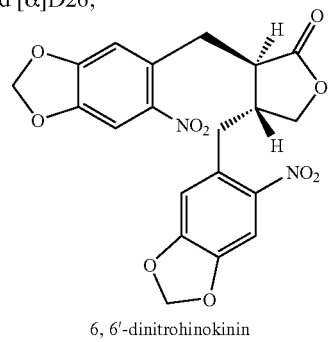

6, 6'-dinitrohinokinin (7)

In the Scheme 1 below, obtaining reactions are illustrated with the corresponding structures of the semi-synthetic derivatives of cubebin (1), isolated from *Piper cubeba* seeds, which consist of the following stages: i; ii; iii; iv and v.

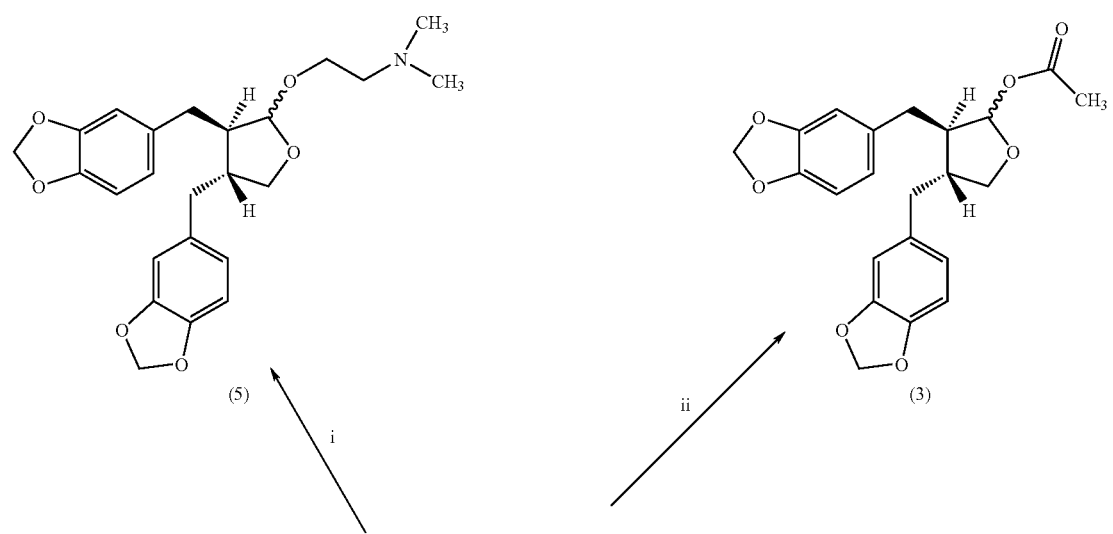
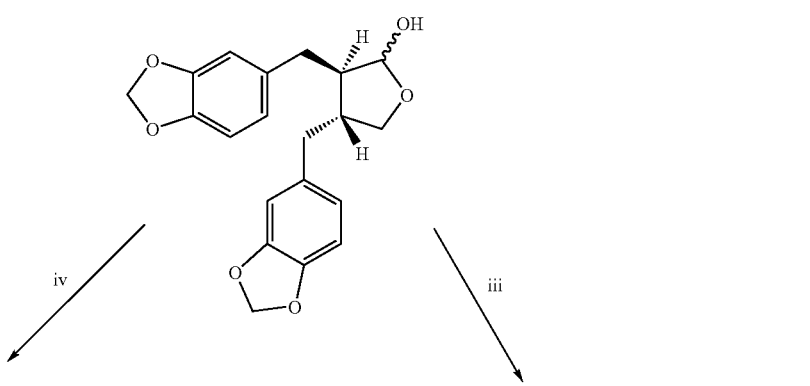
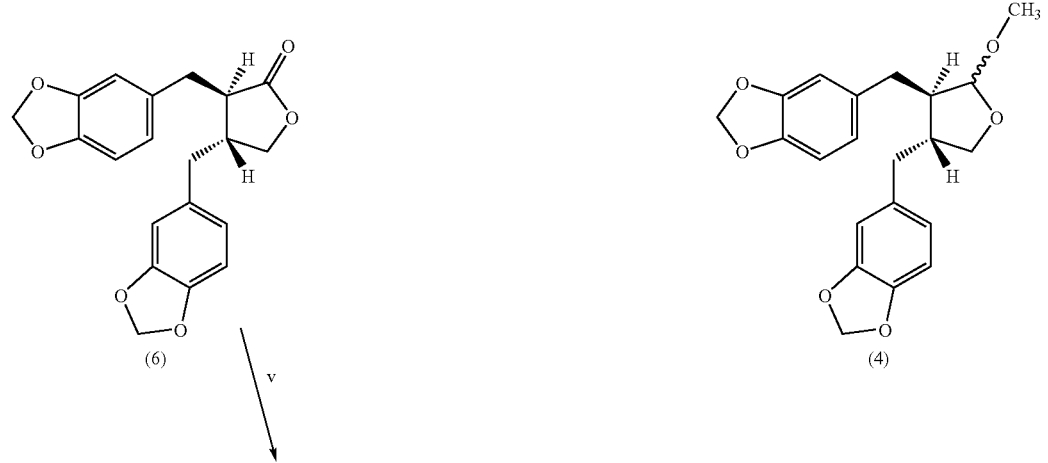

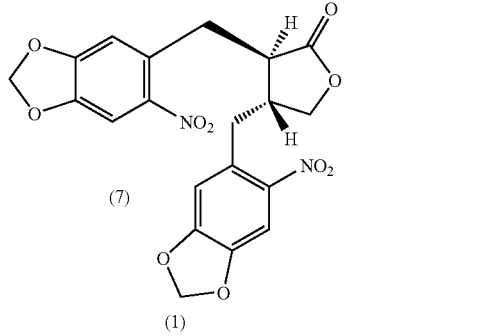

(7)

(1)

Evaluation of the tripanocidal activity was made by checking percentual of lysis from blood tripomastigote forms of different lines of *Trypanosoma cruzi*, isolated from muscles of mice on the parasitemic peak. Biological essays have been made on 200 µl titration microplaques containing about 106 forms of the parasite in each milliliter of used blood. Substance concentrations as used for evaluation were of 10, 25 and 50 µg/ml, which were solubilized under PBS buffer containing 5% dimethyl sulfoxide. After adding substances, infected blood has been incubated at 4° C. under constant shaking for a 24-hour period. After that period, the quantity of parasites surviving to the action of substances was counted in an optical microscope and in comparison to the negative control group (infected blood, adding the solution used to solubilized substances), calculations concerning the determination of lysis percentual have been made. As a positive control, gentian violet has been used under concentration of 250 µg/ml, as indicated for chemoprophylaxis. All essays have been made in triplicate.

The biological activity protocol as described above is already fully published and used in the scientific field, being therefore standardized regarding tripanocidal activity (chemoprophylaxis and susceptibility evaluation for the parasite).

Various scientific works using this method, which is even presented in the original evaluation work for the biological activity of cubebin, as published by Bastos and contributors in 1999.

Results presented by table 1 show the activity of a few cubebin derivatives, as well as their chemoprophylactic and therapeutical potential.

TABLE 1

Results of anti-Chagas evaluation.

| Substances | µg/ml-1/% lysis | | IC50 (µg/ml) |
| --- | --- | --- | --- |
| Cubebin | 25/7.3 | 50/52.3 | 97.6 |
| O-methyl cubebin | 25/13.9 | 50/62.0 | 86.3 |
| O-acetyl cubebin | 25/76.2 | 50/100 | 16.9 |
| Hinokinin | 25/80.1 | 50/95.4 | 0.9 |
| 6,6'-Dinitrohinokinin | 25/57.6 | 50/82.8 | 37.1 |

TABLE 1-continued

Results of anti-Chagas evaluation.

| Substances | µg/ml-1/% lysis | | IC50 (µg/ml) |
| --- | --- | --- | --- |
| Metilpluviatolide | 25/99.0 | 50/100 | 1.30 |
| O-dimethylethylamine cubebin | 25/90.1 | 50/100 | 3.0 |
| Gentian violet | | 250/100 | 76.0 |

For substances bearing 100% activity, treated blood was inoculated into healthy mice with the purpose to verify their chemoprophylactic ability. All substances involved in this assay have shown chemoprophylactic ability.

Besides those, sulfonated (8), halogenated (9), amine (10), amide (11) and glycosylated (12) derivatives, with different substitution standards in both aromatic rings of the backbone with various substituent groups among others, are also object of this application.

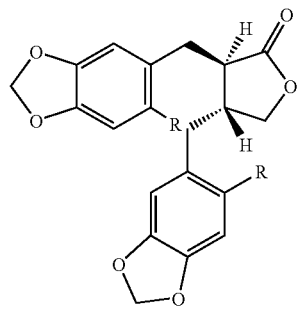

$$R = \begin{cases} -SO_3H & (8) \\ CleF & (9) \\ -NH_2 & (10) \\ -\overset{H}{N}-\overset{O}{\underset{}{C}}-CH_3 & (11) \end{cases}$$

-continued

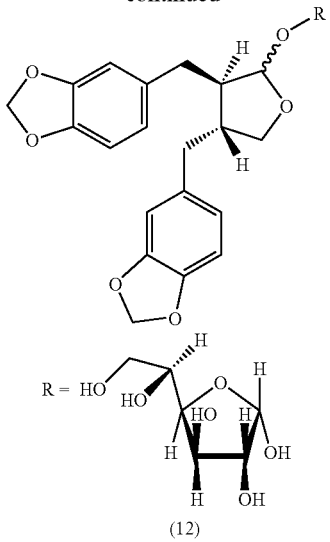

(12)

What is claimed is:

1. A process to obtain a synthetic lignan derivative of structural formula (5):

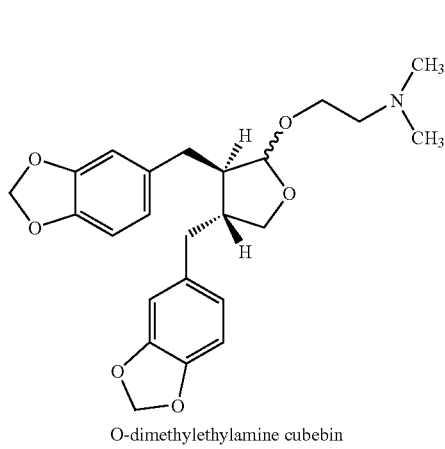

O-dimethylethylamine cubebin from a (−)-cubebin derivative of structural formula (1):

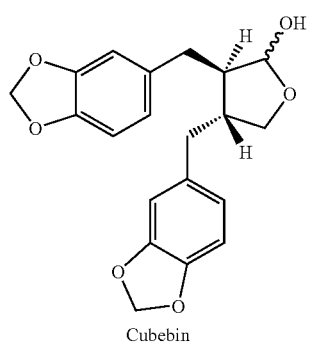

Cubebin comprising the following steps:
a) reacting the (−)-cubebin derivative with sodium ethoxide, followed by addition of dimethylethylamine chloride under reflux to form a reaction medium;
b) adding water and powdered NaHCO$_3$ up to the alkalization point of the reaction medium (pH=9 to 10) followed by extraction with ethyl acetate; and
c) transferring the organic phase of the reaction medium to a collecting flask followed by purification of the synthetic lignan derivative under preparative circular chromatography.

2. A compound having structural formula (5):

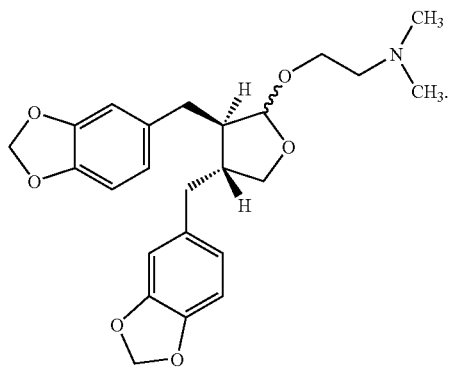

O-dimethylethylamine cubebin (5)

* * * * *